United States Patent
Kang et al.

(10) Patent No.: US 9,089,504 B2
(45) Date of Patent: Jul. 28, 2015

(54) COSMETIC COMPOSITION CONTAINING GREEN TEA COMPONENT

(75) Inventors: Hyun Seo Kang, Yongin-si (KR); Seung Hyun Kang, Yongin-si (KR); Ji Hyun Kim, Yongin-si (KR); Ji Seong Kim, Yongin-si (KR); Yong Joo Na, Yongin-si (KR); Byung Geun Chae, Yongin-si (KR); Sang Hoon Han, Yongin-si (KR)

(73) Assignee: AMOREPACIFIC CORPORATION (KR)

(*) Notice: Subject to any disclaimer, the term of this patent is extended or adjusted under 35 U.S.C. 154(b) by 0 days.

(21) Appl. No.: 14/239,675

(22) PCT Filed: Aug. 20, 2012

(86) PCT No.: PCT/KR2012/006594
§ 371 (c)(1),
(2), (4) Date: Feb. 19, 2014

(87) PCT Pub. No.: WO2013/027984
PCT Pub. Date: Feb. 28, 2013

(65) Prior Publication Data
US 2014/0186315 A1    Jul. 3, 2014

(30) Foreign Application Priority Data
Aug. 24, 2011 (KR) .................. 10-2011-0084701

(51) Int. Cl.
| A61K 8/97 | (2006.01) |
| A61Q 19/08 | (2006.01) |
| A61Q 19/00 | (2006.01) |
| A61K 8/49 | (2006.01) |
| A61Q 19/02 | (2006.01) |

(52) U.S. Cl.
CPC . *A61K 8/97* (2013.01); *A61K 8/498* (2013.01); *A61Q 19/00* (2013.01); *A61Q 19/02* (2013.01); *A61Q 19/08* (2013.01)

(58) Field of Classification Search
IPC .................................................. A61K 8/97, 8/498
See application file for complete search history.

(56) References Cited

U.S. PATENT DOCUMENTS

| 2004/0043085 A1* | 3/2004 | Mautone et al. ........... 424/729 |
| 2006/0286062 A1* | 12/2006 | Schep et al. ............... 424/74 |
| 2013/0078301 A1* | 3/2013 | Constantino .............. 424/450 |

FOREIGN PATENT DOCUMENTS

| JP | 2009507826 A | 2/2009 |
| KR | 100589716 B1 | 6/2006 |
| KR | 100659138 B1 | 12/2006 |
| KR | 1020110023483 A | 3/2011 |
| KR | 1020110031801 A | 3/2011 |

OTHER PUBLICATIONS

International Search Report with English Translation for International Application No. PCT/KR2012/006594 dated Feb. 13, 2013.

\* cited by examiner

*Primary Examiner* — Rosanne Kosson
(74) *Attorney, Agent, or Firm* — Cantor Colburn LLP

(57) ABSTRACT

The present invention provides a cosmetic composition containing one or more selected from a group consisting of green tea saponin and green tea polyphenol as active ingredients. The cosmetic composition of the invention is very safe to the skin and can greatly enhance biological mechanisms in the skin, and thus can serve as an anti-aging cosmetic composition.

11 Claims, 1 Drawing Sheet

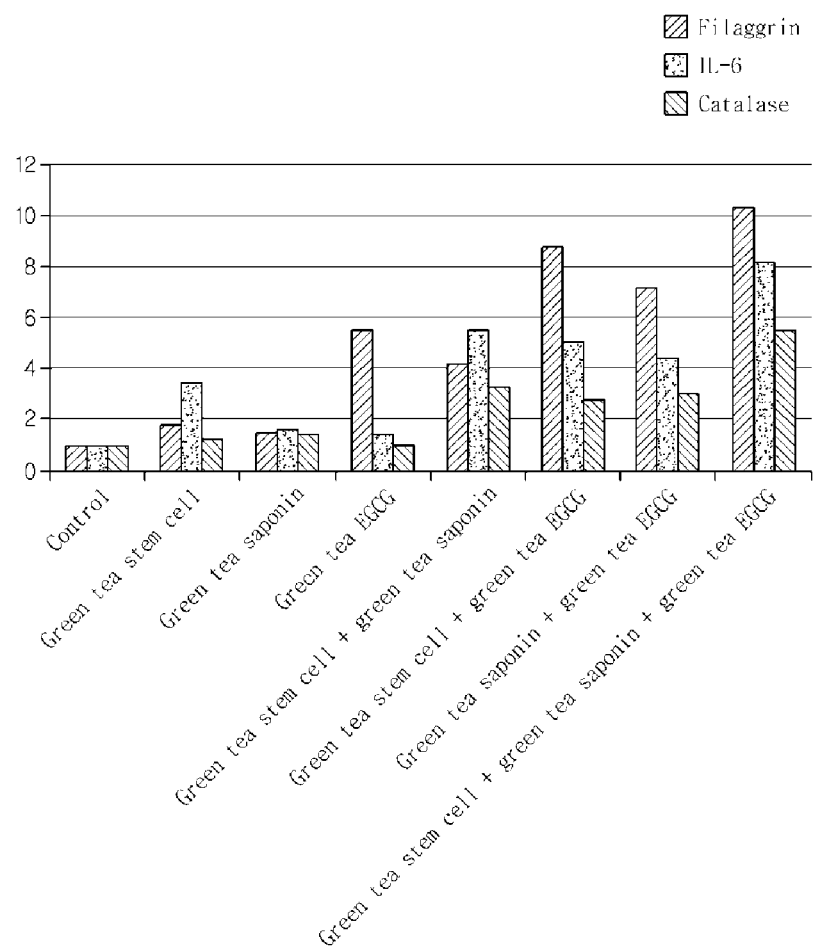

COSMETIC COMPOSITION CONTAINING GREEN TEA COMPONENT

TECHNICAL FIELD

The present disclosure relates to a cosmetic composition containing green tea components.

BACKGROUND ART

Recently, as plant cell culturing techniques using the totipotency of plants are developed, interests in functional secondary metabolites derived from plants are increasing greatly. Since the secondary metabolites are known to have various physiological activities, substances extracted from plant stem cells are drawing attentions as new raw materials of high functional cosmetics. Because this technique allows production of highly functional active substances which occur naturally but are difficult to obtain through chemical synthesis economically, it is expected that new components that could not be used thus far can be developed and utilized. In addition, development of materials using bioprocesses such as the active transformation technology utilizing enzyme treatment is actively carried out. Although needs on functional cosmetics are increasing recently, the development of new functional materials or related technologies is insufficient to satisfy the needs. In this context, cosmetics prepared using the plant stem cell technology, which allows preparation of numerous new functional components, or bioprocesses such as enzyme treatment will draw a lot of attentions with regard to various skin effects, especially anti-aging effect.

SUMMARY OF THE INVENTION

Technical Problem

The inventors of the present disclosure have researched to develop cosmetics containing naturally occurring plant components that do not induce adverse skin reactions and providing excellent anti-aging and anti-wrinkle effects, and have found out that green tea components can provide such effects.

The present disclosure is directed to providing a cosmetic composition exhibiting superior skin safety and excellent skin anti-aging and anti-wrinkle effects by using plant-derived components.

Technical Solution

In a general aspect, there is provided a cosmetic composition containing one or more selected from a group consisting of a green tea saponin and a green tea polyphenol as an active ingredient.

In an exemplary embodiment of the present disclosure, the composition may further contain a green tea stem cell culture product.

In an exemplary embodiment of the present disclosure, the green tea saponin may be one extracted from green tea seed coat and having sugar moieties removed.

In an exemplary embodiment of the present disclosure, the green tea polyphenol may be epigallocatechin gallate (EGCG) extracted from green tea leaf.

In an exemplary embodiment of the present disclosure, the green tea saponin or the green tea polyphenol may be independently contained in an amount of 0.001-1 wt % based on the total weight of the composition.

In an exemplary embodiment of the present disclosure, the stem cell may be one derived from a callus.

In an exemplary embodiment of the present disclosure, the stem cell culture product may be one or more selected from a group consisting of a stem cell line, a lysate thereof, an extract thereof and a culture solution thereof.

In an exemplary embodiment of the present disclosure, the stem cell culture product may be contained in an amount of 0.01-10 wt % based on the total weight of the composition.

In an exemplary embodiment of the present disclosure, the composition may be a composition for anti-aging.

In an exemplary embodiment of the present disclosure, the composition may be a composition for moisturizing skin or strengthening skin barrier function.

In an exemplary embodiment of the present disclosure, the composition may activate the filaggrin gene.

In an exemplary embodiment of the present disclosure, the composition may be a composition for whitening skin or suppressing skin pigmentation.

In an exemplary embodiment of the present disclosure, the composition may activate the interleukin-6 (IL-6) gene.

In an exemplary embodiment of the present disclosure, the composition may be a composition for strengthening skin elasticity or improving skin wrinkles.

In an exemplary embodiment of the present disclosure, the composition may activate the catalase gene.

Advantageous Effects

The cosmetic composition of the present disclosure can be used as a cosmetic composition for anti-aging since it exhibits superior skin safety and provides an excellent of improving biological mechanism in the skin such as activating genes. In addition, since the green tea components used in the present disclosure boost again the activity of genes decreased because of aging and increase the biosynthesis of collagen in a concentration-dependent manner, the green tea components can fundamentally improve the aged skin and provide vitality to the skin with decreased elasticity and gloss by supplying collagen and have an effect that improving skin elasticity as well as preventing skin aging.

DESCRIPTION OF DRAWINGS

FIG. 1 shows the expression level of the filaggrin, interleukin-6 and catalase genes.

DETAILED DESCRIPTION OF THE INVENTION

Mode for Invention

Hereinafter, the present disclosure is described in detail.

Unless defined otherwise, the technical and scientific terms used in the present disclosure have the same meaning as commonly understood by one of ordinary skill in the art.

The present disclosure provides a cosmetic composition containing one or more selected from a group consisting of a green tea saponin and a green tea polyphenol as an active ingredient. The composition may further contain a green tea (*Camellia Sinensis*) stem cell culture product.

The green tea saponin of the present disclosure may be one obtained by extracting a crude saponin of large molecular weight from green tea seed coat and enzymatically removing sugar moieties, thus being easily absorbed to skin and exhibiting high efficiency.

The green tea polyphenol of the present disclosure may be epigallocatechin gallate (EGCG), which is the most abundant in green tea leaf, and may be obtained by extracting green tea leaf with warm water and then solidifying the product as powder.

The green tea saponin or the green tea polyphenol may be independently contained in an amount of 0.001-1 wt %, specifically 0.01-0.5 wt %, based on the total weight of the composition. If the content of each ingredient is below 0.001 wt %, it is difficult to expect skin cell regenerating and antioxidant effects. Further, if the content exceeding 1.0 wt %, an effectiveness of ingredient decreases since the effect is not further increased. Besides, because various solvents have to be combined to stably include the insoluble green tea saponin and polyphenol in a formulation, the value as a cosmetic composition may be degraded.

The green tea stem cell may be obtained by using the recently esteemed plant stem cell culture technique. A totipotent callus derived from the seed, leaf, stem, root, etc. of green tea may be cultured by solid cell culture to establish a stem cell line, from which the active ingredient is mass-produced through suspension cell culture and then extracted.

The culture product may be one or more selected from a group consisting of the derived stem cell line itself, a lysate thereof, an extract thereof and a culture solution thereof. The extract is not particularly limited in extraction method but may be extracted, for example, by culturing a cell line derived from a tissue explant of the plant. In Preparation Example 1 of the present disclosure, a stem cell culture solution obtained from a callus derived from leaf and a lysate of the stem cell line were used. However, the same result as that of the present disclosure may be obtained by using a stem cell line obtained by culturing a callus derived from the embryo, cambium or procambium of green tea, a lysate thereof, an extract thereof or a culture thereof.

The culture product may contain, for example, an amino acid isolated/purified from the green tea stem cell as an active ingredient. The extract used in the present disclosure allows to cope with skin aging fundamentally by boosting again the activity of key genes which is decreased together with skin aging. Further, it provides the effect of improving or reducing wrinkles by increasing elastic fibers in the dermis by increasing collagen synthesis in skin. In addition, it can eliminate reactive oxygen species which are a major cause of skin aging. Accordingly, it can exhibit superior anti-aging effect by resolving the decreased activity of genes, which is the fundamental cause of skin aging, and blocking oxidative stress.

The stem cell culture product may be contained in an amount of 0.01-10 wt %, specifically 0.1-5 wt %, based on the total weight of the composition. If the content is below 0.01 wt %, it is difficult to expect an anti-aging effect through re-activation of genes. Further, if the content exceeding 10 wt %, an effectiveness of ingredient decreases since the effect is not further increased.

The cosmetic composition of the present disclosure may be an composition for anti-aging.

Further, the cosmetic composition of the present disclosure may be a composition for moisturizing skin, strengthening skin barrier function, whitening skin, suppressing skin pigmentation, strengthening skin elasticity, anti-oxidation or improving skin wrinkles.

Human skin contains 3 types of cells. They are keratinocytes which constitute most of the epidermis, melanocytes which produce melanin, and fibroblasts which constitute most of the dermis. The keratinocytes are associated with skin moisturization through prevention of water loss and barrier function of protecting the skin from harmful factors. The melanocytes determine the skin color and tone and, at the same time, are the cause of freckles and blemishes. The fibroblasts produce elastic fibers such as collagen and are associated with skin elasticity and skin wrinkles. According to a genetic study on skin, the genes that show the most significant decrease in activity in the 3 types of cells with aging are: the filaggrin gene for the keratinocytes, the interleukin-6 (IL-6) gene for the melanocytes, and the catalase gene in the fibroblasts. That is to say, these three genes are deeply associated with skin aging.

Filaggrin is a differentiation marker of keratinocytes and is known as a precursor to natural moisturizing factors. Interleukin-6 is a hypomelanogenic factor and is known to inhibit melanin production by melanocytes. Catalase is an enzyme which catalyzes the decomposition of peroxides produced in cells.

The present disclosure is based on the expectation that aged skin can be rejuvenated by activating these three genes.

The composition of the present disclosure activates the filaggrin gene. If the filaggrin gene is activated, the moisturizing effect of suppressing evaporation of water from the skin is improved and the skin barrier effect of protecting the skin from external harmful factors is enhanced.

The composition of the present disclosure activates the interleukin-6 (IL-6) gene. If the IL-6 gene is activated, skin whitening effect is improved since skin color and tone are brightened, and skin pigmentation is suppressed since freckles and blemishes are decreased.

The composition of the present disclosure activates the catalase gene. If the catalase gene is activated, collagen synthesis is promoted, and then skin elasticity is improved and skin wrinkles are improved.

The cosmetic composition of the present disclosure is not particularly limited in formulation. For example, it may be a basic cosmetic, a makeup cosmetic, a hair care cosmetic, a body care cosmetic, etc. and may be selected appropriately depending on purpose.

The cosmetic composition may be formulated into, for example, a solution, a suspension, an emulsion, a paste, a gel, a cream, a lotion, a powder, a soap, a surfactant-containing cleanser, an oil, a powder foundation, an emulsion foundation, a wax foundation, a spray, etc., but is not limited thereto. More specifically, it may be formulated into a basic cosmetic such as softening lotion, nourishing lotion, milk lotion, body lotion, nourishing cream, massage cream, moisturizing cream, hand cream, essence, eye cream, cleansing cream, cleansing foam, cleansing water, pack, gel, patch, oil-in-water (O/W) emulsion, water-in-oil (W/O) emulsion, etc., a coloring cosmetic such as lipstick, makeup base, foundation, etc., a cleanser such as shampoo, rinse, body cleanser, toothpaste, mouthwash, etc., or a hair care cosmetic such as hair tonic, hair fixative such as gel or mousse, hair growth promoter, hairdye, etc.

The cosmetic composition may contain a cosmetically acceptable medium or matrix and may be provided as any topically applicable formulation, e.g., solution, gel, anhydrous solid or paste, oil-in-water emulsion, suspension, microemulsion, microcapsule, microgranule or ionic (liposome) and/or nonionic vesicular dispersion, cream, skin lotion, milk lotion, powder, ointment, spray or conceal stick. These compositions may be prepared according to a method commonly employed in the art.

When the formulation of the present disclosure is solution or emulsion, a solvent, a dissolving agent or an emulsifier may be used as a carrier. For example, water, ethanol, isopropanol, ethyl carbonate, ethyl acetate, benzyl alcohol, benzyl benzoate, propylene glycol, 1,3-butylene glycol, glycerol aliphatic ester, polyethylene glycol or fatty acid ester of sorbitan may be used.

When the formulation of the present disclosure is suspension, a liquid diluent such as water, ethanol or propylene glycol, a suspending agent such as ethoxylated isostearyl alcohol, polyoxyethylene sorbitol ester and polyoxyethylene sorbitan ester, microcrystalline cellulose, aluminum metahydroxide, bentonite, agar, or tragacanth, etc. may be used as a carrier.

When the formulation of the present disclosure is paste, cream or gel, animal oil, vegetable oil, wax, paraffin, starch, tragacanth, cellulose derivatives, polyethylene glycol, silicone, bentonite, silica, talc, or zinc oxide, etc. may be used as a carrier.

When the formulation of the present disclosure is powder or spray, lactose, talc, silica, aluminum hydroxide, calcium silicate or polyamide powder may be used as a carrier. In particular, when the formulation is spray, it may further contain a propellent such as chlorofluorohydrocarbon, propane/butane or dimethyl ether.

When the formulation of the present disclosure is surfactant-containing cleanser, aliphatic alcohol sulfate, aliphatic alcohol ether sulfate, sulphosuccinic acid monoester, isethionate, imidazolinium derivatives, methyltaurate, sarcosinate, fatty acid amide ether sulfate, alkylamidobetain, aliphatic alcohol, fatty acid glyceride, fatty acid diethanolamide, vegetable oil, lanolin derivatives, or ethoxylated glycerol fatty acid ester, etc. may be used as a carrier.

The cosmetic composition of the present disclosure may further contain a thickener. The thickener contained in the cosmetic composition of the present disclosure may be methyl cellulose, carboxymethyl cellulose, carboxymethyl hydroxyguanine, hydroxymethyl cellulose, hydroxyethyl cellulose, carboxyvinyl polymer, polyquaternium, cetearyl alcohol, stearic acid, carrageenan, etc. Specifically, one or more selected from a group consisting of carboxymethyl cellulose, carboxyvinyl polymer and polyquaternium may be used. Most specifically, carboxyvinyl polymer may be used.

In an exemplary embodiment of the present disclosure, the cosmetic composition may contain various adequate matrices and additives as desired and their kind and amount can be easily determined by those skilled in the art. The cosmetic composition may contain acceptable additives such as preservative, colorant, additives etc. commonly used in the art. Specifically, the preservative may be phenoxyethanol, 1,2-hexanediol, etc. and a synthetic fragrance may be used.

Further, the cosmetic composition of the present disclosure may contain a substance selected from a group consisting of water-soluble vitamin, oil-soluble vitamin, polypeptide, polysaccharide, sphingolipid and seaweed extract. In addition, it may further contain oil, fat, humectant, emollient, surfactant, organic or inorganic pigment, organic powder, UV absorbent, preservative, sterilizer, antioxidant, plant extract, pH control agent, alcohol, colorant, fragrance, blood circulation stimulant, cooling agent, antiperspirant, purified water, etc.

However, the ingredients that may be contained in the cosmetic composition are not limited thereto. And, the amount of the ingredients may be determined within the range not negatively affecting the purpose and effect of the present disclosure.

Hereinafter, the present disclosure will be described in detail through examples. However, the following examples are for illustrative purposes only and it will be apparent to those of ordinary skill in the art that the scope of the present disclosure is not limited by the examples.

Preparation Example 1

Extraction of Active Ingredients

A callus was induced by cutting the leaf of green tea and cultivating in a callus inducing medium (Table 1). A callus began to be induced after 15 days and a callus layer began to be separated after 30 days. After the callus layer was separated, a white and soft portion showing good growth rate was sub-cultured with 21-day intervals using a fresh medium which is the same as the inducing medium. The composition of the callus inducing medium is shown in Table 1. Auxin was added at a concentration of 1-3 mg/L to the medium as a growth regulator. The cultivation was performed in a dark room maintained at 25±1° C.

TABLE 1

|  | Composition | Content (mg/L) |
| --- | --- | --- |
| Inorganic salts | $KNO_3$ | 1011.1 |
|  | $MgSO_4 \cdot 7H_2O$ | 121.56 |
|  | $MnSO_4 \cdot 4H_2O$ | 10 |
|  | $ZnSO_4 \cdot 7H_2O$ | 2 |
|  | $CuSO_4 \cdot 5H_2O$ | 0.025 |
|  | $CaCl_2 \cdot 2H_2O$ | 113.23 |
|  | KI | 0.75 |
|  | $CoCl_2 \cdot 6H_2O$ | 0.025 |
|  | $NaH_2PO_4 \cdot H_2O$ | 130.44 |
|  | $H_3BO_3$ | 3 |
|  | $Na_2MoO_4 \cdot 2H_2O$ | 0.25 |
|  | FeNaEDTA | 36.7 |
| Vitamins | Myo-inositol | 450 |
|  | Thiamine•HCl | 20 |
|  | Nicotinic acid | 2 |
|  | Pyridoxine•HCl | 2 |
|  | L-Ascorbic acid | 100 |
|  | Citric acid | 150 |
| Plant hormones | Auxin | 1-3 |
|  | Gibberellic acid | 0.5 |
| Amino acid | Casein hydrolysate | 500 |
|  | Sucrose | 30,000 |
|  | Activated carbon | 100 |
|  | Gelrite | 4,000 |

The callus was cultivated in a solid medium (Guchefa) and a stem cell line stably growing therefrom was selected. The solid medium used in the present disclosure is an MS medium with very high contents of $NO_3$—N, $NH_4$—N and K when compared with other media. The composition of the solid medium is shown in Table 2.

TABLE 2

|  | Composition | Content (mg/L) |
| --- | --- | --- |
| Inorganic salts | $NH_4NO_3$ | 1650 |
|  | $H_3BO_3$ | 6.2 |
|  | $CaCl_2$ | 332.2 |
|  | $CoCl_2 \cdot 6H_2O$ | 0.025 |
|  | $CuSO_4 \cdot 5H_2O$ | 0.025 |
|  | Na 2-EDTA | 37.26 |
|  | $FeSO_4 \cdot 7H_2O$ | 27.8 |
|  | $MgSO_4$ | 180.7 |
|  | $MnSO_4(H_2O)$ | 16.9 |
|  | $Na_2MoO_4 \cdot 2H_2O$ | 0.25 |
|  | KI | 0.83 |
|  | $KNO_3$ | 1900 |
|  | $KH_2PO_4$ | 170 |
|  | $ZnSO_4 \cdot 7H_2O$ | 8.6 |
| Vitamins | Myo-inositol | 100 |
|  | Nicotinic acid | 0.5 |
|  | Pyridoxine•HCl | 0.5 |
|  | Thiamine•HCl | 0.1 |
| Amino acid | Glycine | 2 |

The selected stem cell line was cultivated in a suspension medium containing sugar and growth hormones (Table 3). The composition of the suspension medium used for cultivating the stem cell line is shown in Table 3.

TABLE 3

| | Composition | Content (mg/L) |
|---|---|---|
| Inorganic salts | $KNO_3$ | 1011.1 |
| | $MgSO_4 \cdot 7H_2O$ | 121.56 |
| | $MnSO_4 \cdot 4H_2O$ | 10 |
| | $ZnSO_4 \cdot 7H_2O$ | 2 |
| | $CuSO_4 \cdot 5H_2O$ | 0.025 |
| | $CaCl_2 \cdot 2H_2O$ | 113.23 |
| | KI | 0.75 |
| | $CoCl_2 \cdot 6H_2O$ | 0.025 |
| | $NaH_2PO_4 \cdot H_2O$ | 130.44 |
| | $H_3BO_3$ | 3 |
| | $Na_2MoO_4 \cdot 2H_2O$ | 0.25 |
| | FeNaEDTA | 36.7 |
| Vitamins | Myo-inositol | 200 |
| | Thiamine•HCl | 20 |
| | Nicotinic acid | 2 |
| | Pyridoxine•HCl | 2 |
| | L-Ascorbic acid | 100 |
| | Citric acid | 150 |
| Plant hormones | Auxin | 1-3 |
| | Gibberellic acid | 0.1 |
| Amino acids | Aspartic acid | 133 |
| | Arginine | 175 |
| | Proline | 115 |
| | Glycine | 75 |
| | Sucrose | 20,000 |

From the cells cultivated in the suspension medium, a mixture of various active ingredients was obtained. Additionally, the cell wall of the cultivated cells was disrupted and components eluted therefrom were also obtained.

A green tea saponin was obtained by extracting the seed coat of green tea and then treating with enzymes. A green tea polyphenol was obtained by repeating a procedure of extracting the leaf of green tea with warm water and concentrating same. As a result, highly pure EGCG was obtained.

Test Example 1

Effect of Promoting Collagen Synthesis

Human fibroblasts were cultured in a 24-well culture plate and the culture medium was replaced with one containing an extraction mixture extracted from the green tea stem cell at a concentration of 10 ppm (Reference Example 1), 5 ppm (Reference Example 2), 1 ppm (Reference Example 3) or 0 ppm (Comparative Example 1), respectively. On day 3, after adding 0.5 mL of Dulbecco's modified Eagle's medium (DMEM) containing 10% fetal bovine serum per each well, 10 µCi of L-[2,3,4,5-$^3$H]-proline was added. 24 hours later, the medium and cells in each well were collected and washed with 5% trichloroacetic acid (TCA) solution. A test tube of Comparative Example 1 was kept at 4° C., and test tubes of Reference Examples and Examples containing phenylpropanoid at different concentrations were incubated at 37° C. for 90 minutes after adding 1 unit/µL type I collagenase. Subsequently, after adding 0.05 mL of 50% trichloroacetic acid to all the test tubes and allowing to stand at 4° C. for 20 minutes, centrifugation was carried out at 12,000 rpm for 10 minutes. Counts per minute (CPM) for each supernatant and precipitant were measured using a liquid scintillation counter (LSC) and relative collagen biosynthesis (RCB) for Reference Examples and Comparative Example 1 was calculated according to Equation 1. The result is shown in Table 4.

$$RCB(\%) = (CPM \text{ for collagen})/[(CPM \text{ for total collagen} - CPM \text{ for collagen}) \times 5.4 + CPM \text{ for collagen}] \times 100 \quad \text{[Equation 1]}$$

TABLE 4

| | Green tea stem cell extract (ppm) | Relative collagen biosynthesis (RCB) (%) |
|---|---|---|
| Reference Example 1 | 10 | 180 |
| Reference Example 2 | 5 | 149 |
| Reference Example 3 | 1 | 122 |
| Comparative Example 1 | 0 | 100 |

As can be seen from Table 4, the extraction mixture extracted from the green tea stem cell increased the collagen biosynthesis by fibroblasts in a concentration-dependent manner.

Table 5 shows a result of measuring relative collagen biosynthesis (RCB) for green tea saponin (Example 1), green tea polyphenol (Example 2), a mixture of green tea stem cell and green tea saponin (Example 3), a mixture of green tea stem cell and green tea polyphenol (Example 4), a mixture of green tea saponin and green tea polyphenol (Example 5) and a mixture of green tea stem cell, green tea saponin and green tea polyphenol (Example 6).

TABLE 5

| | Green tea component extract (ppm) | Relative collagen biosynthesis (RCB) (%) |
|---|---|---|
| Comparative Example 1 | 0 (none) | 100 |
| Reference Example 1 | Green tea stem cell (10 ppm) | 180 |
| Example 1 | Green tea saponin (1 ppm) | 140 |
| Example 2 | Green tea EGCG (10 ppm) | 135 |
| Example 3 | Green tea stem cell + green tea saponin | 235 |
| Example 4 | Green tea stem cell + green tea EGCG | 215 |
| Example 5 | Green tea saponin + green tea EGCG | 190 |
| Example 6 | Green tea stem cell + green tea saponin + green tea EGCG | 270 |

Test Example 2

Effect of Activating Genes

To investigate the effect of green tea stem cell, green tea saponin and green tea polyphenol in skin cells, normal human keratinocytes (NHK) and normal human fibroblasts (NHF) were used. The fibroblasts were acquired from a replicative senescence model wherein cell aging was induced through repeated sub-culturing.

For genes to be tested, filaggrin and interleukin-6 were selected for keratinocytes, and catalase for fibroblasts.

Green tea stem cell, green tea saponin and green tea polyphenol were tested at concentrations below that exhibiting 80% or more of cell viability after carrying out cytotoxicity test for each cell. After treating with green tea stem cell, green tea saponin and green tea polyphenol, the cells were collected 24 hours later and washed twice with 10 mL of phosphate buffered saline (PBS). Then, total RNA was isolated from the cell using the TRIzol reagent (Invitrogen, Carlsbad, Calif., USA). The isolated RNA was purified once again using the Qiagen RNeasy kit (Qiagen, Valencia, Calif.) and cDNA was synthesized therefrom using the Superscript Reverse Transcriptase (RT) II kit (Invitrogen, Carlsbad, Calif.). Then, change in the expression of the filaggrin, interleukin-6 and catalase genes was quantitatively analyzed by real-time reverse transcription polymerase chain reaction (Q-RT-PCR). The change in the gene expression pattern was evaluated using the TaqMan® gene expression assay kit (Applied Biosystems, Foster City, Calif.). The used primers were: Hs00856927_g1 for filaggrin; Hs00174360_m1 for interleukin-6; and Hs00156308_m1 for catalase. The expression of filaggrin, interleukin-6 and catalase in the cells analyzed by real-time PCR is shown in Table 6.

TABLE 6

|  |  | Filaggrin | IL-6 | Catalase |
|---|---|---|---|---|
| Comparative Example 2 | Control (none) | 1 | 1 | 1 |
| Example 4 | Green tea stem cell (100 ppm) | 1.8 | 3.5 | 1.2 |
| Example 5 | Green tea saponin (1 ppm) | 1.5 | 1.6 | 1.4 |
| Example 6 | Green tea EGCG (10 ppm) | 5.5 | 1.4 | 1.0 |
| Example 7 | Green tea stem cell + green tea saponin | 4.2 | 5.5 | 3.3 |
| Example 8 | Green tea stem cell + green tea EGCG | 8.8 | 5.1 | 2.8 |
| Example 9 | Green tea saponin + green tea EGCG | 7.2 | 4.4 | 3.0 |
| Example 10 | Green tea stem cell + green tea saponin + green tea EGCG | 10.3 | 8.2 | 5.5 |

As seen from Table 6, green tea stem cell culture product (Example 4), green tea saponin (Example 5) and green tea EGCG (Example 6) increased the expression of the genes. Particularly, the green tea stem cell increased the expression of the IL-6 gene, the green tea saponin increased the expression of the catalase gene, and the green tea EGCG was effective in increasing the expression of the filaggrin gene. When these components were used in combination (Examples 7-10), a synergic effect was achieved when two or components were combined, and, an optimal anti-aging effect could be achieved in the gene level when all the three components were combined (Example 10). The expression level described in Table 6 is graphically shown in FIG. 1.

Test Example 3

Skin Safety Test

To evaluate skin safety of the cosmetic composition for anti-aging according to the present disclosure, irritation to skin was measured for Formulation Example 2.

The measurement was made in the Department of Dermatology, Chungbuk National University Hospital. The cosmetic composition of Formulation Example 2 was applied on the backs of thirty healthy adults with an average age of 33.2 years for 48 hours and skin response was monitored for 24 hours. Skin irritation was evaluated according to the CTFA guideline (1981) and the evaluation standard of Frosch & Kligman.

No skin irritation was found in the thirty adults to whom the cosmetic composition of the present disclosure (Formulation Example 2) was applied. Accordingly, it can be seen that the cosmetic composition of the present disclosure has very superior skin safety.

Hereinafter, the present disclosure will be described in detail through formulation examples. However, the following formulation examples are for illustrative purposes only and it will be apparent to those of ordinary skill in the art that the scope of the present disclosure is not limited by the formulation examples.

Formulation Example 1

Softening Lotion (Skin Lotion)

Softening lotion was prepared with the composition described in Table 7 according to a commonly employed method.

TABLE 7

| Ingredients | Contents (wt %) |
|---|---|
| Green tea stem cell culture product | 1.0 |
| Green tea saponin | 0.1 |
| Green tea polyphenol | 0.1 |
| Glycerin | 3.5 |
| Oleyl alcohol | 1.5 |
| Ethanol | 5.5 |
| Polysorbate 80 | 3.2 |
| Carboxyvinyl polymer | 1.0 |
| Butylene glycol | 2.0 |
| Propylene glycol | 2.0 |
| Preservative and fragrance | adequate |
| Purified water | balance |
| Total | 100 |

Formulation Example 2

Nourishing Lotion (Milk Lotion)

Nourishing lotion was prepared with the composition described in Table 8 according to a commonly employed method.

TABLE 8

| Ingredients | Contents (wt %) |
|---|---|
| Green tea stem cell culture product | 1.0 |
| Green tea saponin | 0.1 |
| Green tea polyphenol | 0.1 |
| Glycerin | 3.0 |
| Butylene glycol | 3.0 |
| Propylene glycol | 3.0 |
| Carboxyvinyl polymer | 0.1 |
| Beeswax | 4.0 |
| Polysorbate 60 | 1.5 |
| Caprylic/capric triglyceride | 5.0 |
| Squalane | 5.0 |
| Sorbitan sesquioleate | 1.5 |
| Cetearyl alcohol | 1.0 |
| Triethanolamine | 0.2 |
| Preservative and fragrance | adequate |
| Purified water | balance |
| Total | 100 |

Formulation Example 3

Nourishing Cream

Nourishing cream was prepared with the composition described in Table 9 according to a commonly employed method.

TABLE 9

| Ingredients | Contents (wt %) |
| --- | --- |
| Green tea stem cell culture product | 1.0 |
| Green tea saponin | 0.1 |
| Green tea polyphenol | 0.1 |
| Glycerin | 3.5 |
| Butylene glycol | 3.0 |
| Liquid paraffin | 7.0 |
| β-Glucan | 7.0 |
| Carbomer | 0.1 |
| Caprylic/capric triglyceride | 3.0 |
| Squalane | 5.0 |
| Cetearyl glucoside | 1.5 |
| Sorbitan stearate | 0.4 |
| Polysorbate 60 | 1.2 |
| Triethanolamine | 0.1 |
| Preservative and fragrance | adequate |
| Purified water | balance |
| Total | 100 |

Formulation Example 4

Massage Cream

Massage cream was prepared with the composition described in Table 10 according to a commonly employed method.

TABLE 10

| Ingredients | Contents (wt %) |
| --- | --- |
| Green tea stem cell culture product | 1.0 |
| Green tea saponin | 0.1 |
| Green tea polyphenol | 0.1 |
| Glycerin | 8.0 |
| Butylene glycol | 3.0 |
| Liquid paraffin | 45.0 |
| β-Glucan | 7.0 |
| Carbomer | 0.1 |
| Caprylic/capric triglyceride | 3.0 |
| Beeswax | 4.0 |
| Cetearyl glucoside | 1.5 |
| Sorbitan sesquioleate | 0.9 |
| Paraffin | 1.5 |
| Preservative, colorant and fragrance | adequate |
| Purified water | balance |
| Total | 100 |

Formulation Example 5

Pack

Pack was prepared with the composition described in Table 11 according to a commonly employed method.

TABLE 11

| Ingredients | Contents (wt %) |
| --- | --- |
| Green tea stem cell culture product | 1.0 |
| Green tea saponin | 0.1 |
| Green tea polyphenol | 0.1 |
| Glycerin | 4.0 |
| Polyvinyl alcohol | 15.0 |
| Hyaluronic acid extract | 5.0 |
| β-Glucan | 7.0 |
| Allantoin | 0.1 |
| Nonyl phenyl ether | 0.4 |
| Polysorbate 60 | 1.2 |
| Ethanol | adequate |
| Preservative and fragrance | adequate |
| Purified water | balance |
| Total | 100 |

While the exemplary embodiments have been shown and described, it will be understood by those skilled in the art that various changes in form and details may be made thereto without departing from the spirit and scope of this disclosure as defined by the appended claims.

In addition, many modifications can be made to adapt a particular situation or material to the teachings of this disclosure without departing from the essential scope thereof. Therefore, it is intended that this disclosure not be limited to the particular exemplary embodiments disclosed as the best mode contemplated for carrying out this disclosure, but that this disclosure will include all embodiments falling within the scope of the appended claims.

The invention claimed is:

1. A cosmetic composition comprising a combination of a green tea saponin and a green tea polyphenol as an active ingredient in a therapeutically effective amount, and further comprising a therapeutically effective amount of a green tea stem cell culture product.

2. The cosmetic composition according to claim 1, wherein the green tea saponin is one extracted from green tea seed coat and having sugar moieties removed.

3. The cosmetic composition according to claim 1, wherein the green tea polyphenol is epigallocatechin gallate (EGCG) extracted from green tea leaf.

4. The cosmetic composition according to claim 1, wherein a concentration of the green tea saponin is 0.001-1 wt % based on the total weight of the composition, and a concentration of the green tea polyphenol is 0.001-1 wt % based on the total weight of the composition.

5. The cosmetic composition according to claim 1, wherein the stem cell is one derived from a callus.

6. The cosmetic composition according to claim 1, wherein the stem cell culture product is one or more selected from a group consisting of a stem cell line, a lysate thereof, an extract thereof and a culture solution thereof.

7. The cosmetic composition according to claim 1, wherein the stem cell culture product is contained in an amount of 0.01-10 wt % based on the total weight of the composition.

8. A method comprising transdermally administering the cosmetic composition according to claim 1 to a subject in such need, wherein the method is for improving the skin,
wherein the improving the skin is anti-skin aging, moisturizing skin, strengthening skin barrier function, whitening skin, suppressing skin pigmentation, strengthening skin elasticity or improving skin wrinkles.

9. The method according to claim 8, wherein the method for moisturizing skin or strengthening skin barrier function activates the filaggrin gene.

10. The method according to claim 8, wherein the method for whitening skin or suppressing skin pigmentation activates the interleukin-6 (IL-6) gene.

11. The method according to claim 8, wherein the method for strengthening skin elasticity or improving skin wrinkles activates the catalase gene.

* * * * *